(12) United States Patent
Guenter et al.

(10) Patent No.: US 8,864,494 B2
(45) Date of Patent: Oct. 21, 2014

(54) HOLDING PIECE FOR AN IMPLANT

(75) Inventors: Daniel Guenter, Basel (CH); Rainer Bammerlin, Basel (CH); Frank Kenk, Basel (CH); Guillaume Bugnard, Basel (CH); Frederic Blason, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 13/387,146

(22) PCT Filed: Jul. 27, 2010

(86) PCT No.: PCT/EP2010/004583
§ 371 (c)(1),
(2), (4) Date: Mar. 27, 2012

(87) PCT Pub. No.: WO2011/012284
PCT Pub. Date: Feb. 3, 2011

(65) Prior Publication Data
US 2012/0171638 A1    Jul. 5, 2012
US 2014/0227661 A2    Aug. 14, 2014

(30) Foreign Application Priority Data

Jul. 27, 2009    (EP) .................................... 09009674

(51) Int. Cl.
*A61C 8/00*    (2006.01)
(52) U.S. Cl.
CPC ........... *A61C 8/0087* (2013.01); *A61C 2202/00* (2013.01); *A61C 8/0089* (2013.01)
USPC .......................................... 433/141; 433/172
(58) Field of Classification Search
USPC ................... 433/141, 172, 173, 174
See application file for complete search history.

(56) References Cited

U.S. PATENT DOCUMENTS

| 6,217,332 | B1 * | 4/2001 | Kumar | 433/173 |
| 6,261,097 | B1 | 7/2001 | Schmutz | |
| 6,315,562 | B1 * | 11/2001 | Kumar | 433/173 |
| 6,416,324 | B1 * | 7/2002 | Day | 433/173 |
| 6,561,805 | B2 * | 5/2003 | Kumar | 433/174 |
| 7,160,109 | B2 * | 1/2007 | Gervais et al. | 433/141 |

(Continued)

FOREIGN PATENT DOCUMENTS

EP         1749501        7/2007
WO    WO 2009/123798 A1    10/2009

OTHER PUBLICATIONS

Jan. 28, 2011 International Search Report and Written Opinion in PCT/US2010/004583.

*Primary Examiner* — Ralph Lewis
(74) *Attorney, Agent, or Firm* — Novak Druce Connolly Bove + Quigg LLP

(57) ABSTRACT

A housing (35) for an implant (25), a holding piece (1) to connect the implant (25) to the housing (35), and an insertion tool (20) for inserting the implant (25) into an implant site. The holding piece (1) includes at least one resilient element (45) for detachably connecting to the implant (25) with a first retentive force and a tool retention means to connect to the insertion tool (20) with a second retentive force which is greater than the first retentive force. In between the two ends the holding piece (1) features a housing connection segment (30) for connecting the holding piece (1) to the housing (35). On a distal end the insertion tool (20) comprises torque transmission means, which transmit torque directly to the holding piece (1) and/or to the implant (25).

20 Claims, 9 Drawing Sheets

(56) References Cited

U.S. PATENT DOCUMENTS

| | | | |
|---|---|---|---|
| 7,887,325 B2* | 2/2011 | Whipple | 433/163 |
| 2002/0177105 A1* | 11/2002 | Engman | 433/173 |
| 2004/0172035 A1 | 9/2004 | Parmigiani | |
| 2006/0029907 A1 | 2/2006 | Linder | |
| 2006/0217738 A1 | 9/2006 | Tanimura | |
| 2006/0269890 A1 | 11/2006 | Mundwiler | |
| 2008/0154281 A1 | 6/2008 | Schaffran | |

* cited by examiner

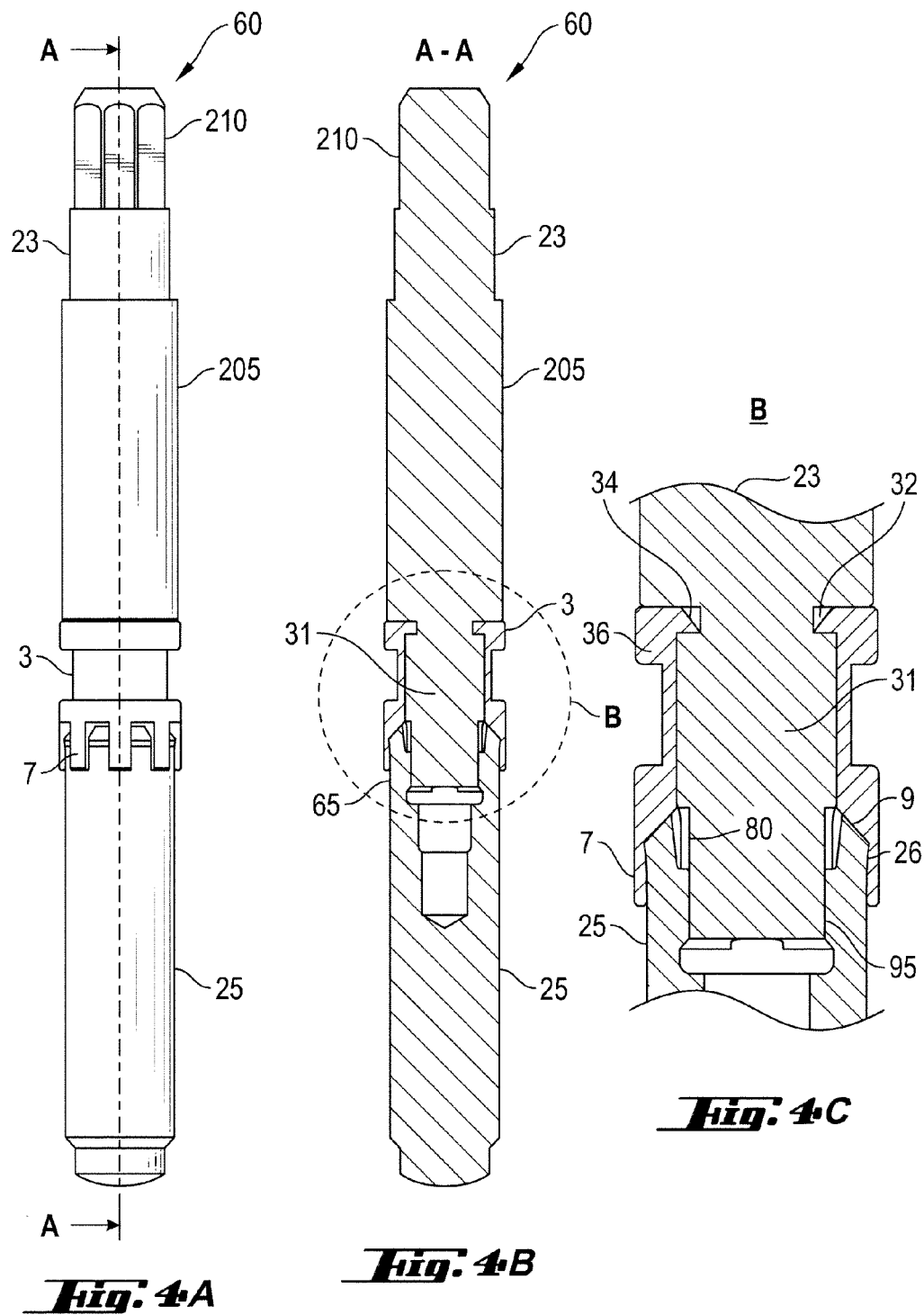

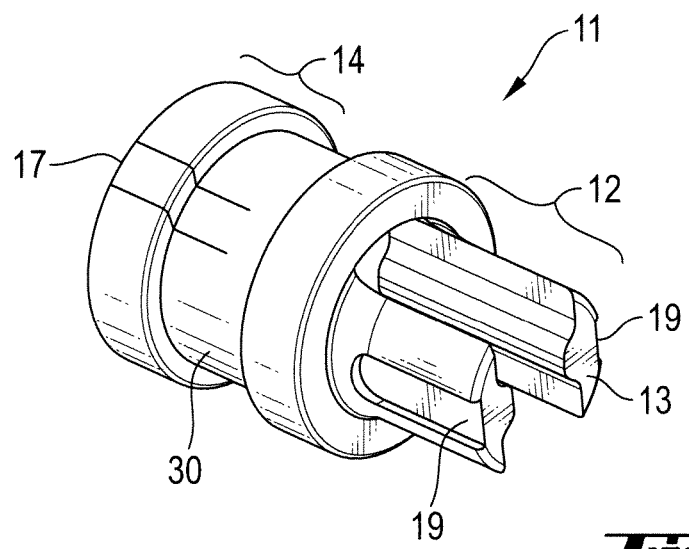
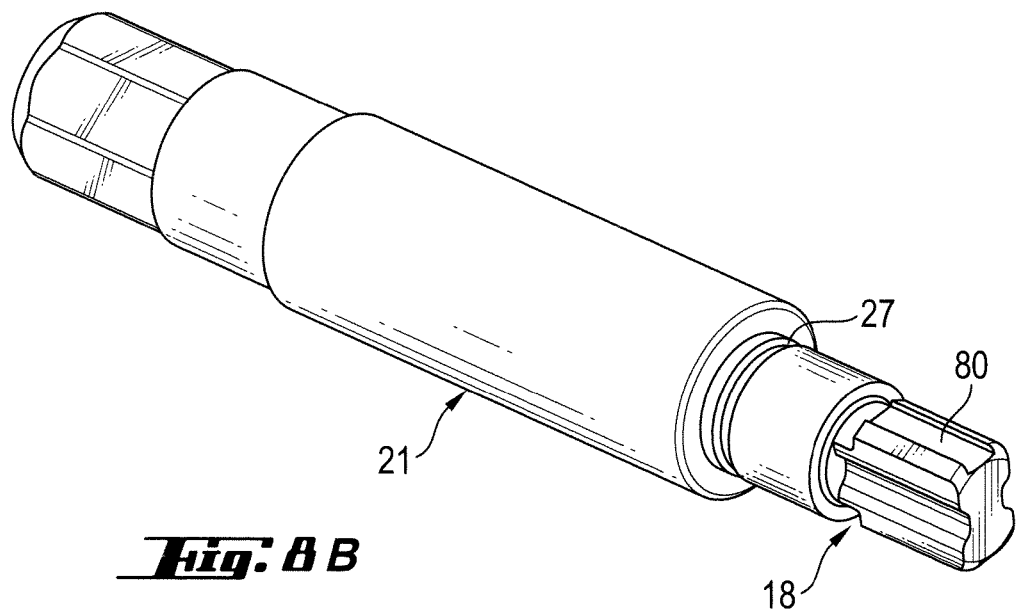

HOLDING PIECE FOR AN IMPLANT

FIELD OF THE INVENTION

The present invention relates to a holding piece for a medical tool, in particular a dental implant.

BACKGROUND

Prior to application or implantation medical tools must be sterilized. In order to reduce the risk of contamination the number of handling steps of sterilized products should be kept to a minimum. Therefore medical tools are often sterilized together with the housing in which they are delivered or stored. The housings should allow easy access of the sterilizing agent (vapour, liquid or radiation) to the product to be sterilized. Furthermore, the housing should protect the medical tool from physical damage. Some medical products are very sensitive to abrasion due to contact with other surfaces, especially in combination with vibration, which often occurs during transportation.

This is particularly true in relation to dental implants, which are inserted into the jaw bone to replace one or more teeth. The surface of these implants, particularly those parts of the implant which will, in use, be positioned within the bone, are often treated to enhance tissue adhesion. Such treated surfaces are very sensitive to abrasion or deterioration when placed in contact with other surfaces.

To minimize abrasion and other deteriorating interactions with any surface, housings have been developed in which the medical tools, such as implants, can be firmly attached to the body of the housing for transportation and storage. Housings are known which firmly hold the implant at specified areas in such a way that the majority of the implant is held away from the interior of the housing.

U.S. Pat. No. B1 6,261,097 discloses a housing including a holding device which comprises a sleeve and a carrier screw, one end of which can be screwed into the internally threaded bore of an implant. The sleeve of the holding device serves to fix the implant inside an ampoule such that the implant itself does not contact the ampoule walls. The opposing end of the screw is shaped for connection to a screwing-in, or insertion, tool for removal of the implant from the housing and implantation.

The sleeve is in contact with the body of the housing during transportation. Prior to insertion of the implant the carrier screw is connected to an insertion tool. The arrangement consisting of implant/sleeve/carrier screw/insertion tool is then removed from the housing. With the aid of the insertion tool the implant is then screwed into a cavity in the bone. The carrier screw therefore provides means to transmit torque from the insertion tool to the implant. After the implant has been screwed into the bone the carrier screw is detached from the implant. For this step the practitioner reverses the direction of rotation of the insertion tool.

A disadvantage of this system is that the carrier screw might not easily be removed from the implant as force is applied to the carrier screw during insertion of the implant, which connects the carrier screw tightly to the implant. Therefore, special care has to be taken when unscrewing the carrier screw from the implant not to loosen the connection of the implant to the bone. This requires the use of an additional tool to steady the implant during initial loosening of the carrier screw. The need to unscrew the carrier screw to remove the holding element presents an additional, undesirable step in the implantation procedure.

Furthermore, a holding piece comprising two components creates greater manufacturing costs and complexity.

HP-A1-1 749 501 describes a holding element for a dental implant including an engagement section for connection to an insertion tool, a retention section adapted for engagement with a housing and a clamping member for connecting the holding element to the dental implant. The clamping member lockingly engages the implant when the clamping member is in a non-compressed position. The holding element can thus be removed from the implant after insertion simply by compressing the clamping member without the need for an unscrewing motion. However the holding element must still be connected to a separate insertion tool in order to insert the implant. Therefore after insertion both the insertion tool and the holding piece must be removed from the implant.

The holding element further comprises a force transmission element, which co-operates with the internal structure of the implant in order to transmit a torque to the implant. The holding element must therefore be strong enough to withstand the torque placed on it during use and to transmit this effectively to the implant. Therefore the holding element is often made from titanium or another metal material via machining.

The cost of production of this type of holding element is therefore high. As the holding element is used to hold the implant within the packaging a separate holding element must be manufactured for each implant. This increases the cost of production of each implant.

Insertion tools which connect directly to the implant are also known. These can be multiple use tools which are provided to the surgery separately from the implant or single use tools supplied within the implant housing. Although this overcomes the problem of having two separate elements connected to the implant during insertion, the use of a directly connecting insertion tool results in new problems. When the insertion tool is provided in the packaging the above discussed problem of high manufacturing expense remains. When the tool is provided separately an alternative solution to the problem of securely holding the implant within the packaging must be found.

SUMMARY OF THE INVENTION

The problem of the present invention is to provide a holding piece for an implant, which simplifies the insertion procedure for the implant and reduces the cost of the holding piece, as well as a housing and insertion tool in connection with said holding piece.

The holding piece according to a first aspect of the present invention comprises a first end and a second end, both ends arranged on a longitudinal axis, and in between the two ends a housing connection segment for connecting the holding piece to a housing for the implant. The first end comprises at least one resilient element for connecting to an implant, said at least one resilient element adapted to retain the implant with a first retentive force. The holding piece further comprises tool retention means adapted to directly connect the holding piece to an insertion tool with a second retentive force that is greater than the first retentive force.

The tool retention means of the holding piece is adapted to directly cooperate with an insertion tool, that is no further pieces or tools, such as carrier screws, are required to connect the insertion tool to the holding piece. Typically, the insertion tool is temporarily connected to the holding piece for the process of removing the implant from the housing, transferring the implant to the implant site and inserting the implant into the bone. In this way the insertion tool can be a multiple use tool which is supplied separately from the implant.

The holding piece has a dual connection function. The at least one resilient element connects to an implant and the tool retention means connects to an insertion tool. Therefore, in one sense, the holding piece acts as an adaptor, which allows an implant to be connected to an insertion tool. The holding piece provides all the necessary features to firmly connect to an implant and to an insertion tool at the same time. No carrier screw or other additional items are needed to form the two connections. Therefore, the production of the holding piece according to the present invention is greatly simplified. In addition the holding piece enables the implant to be indirectly held within the housing, via the housing connection segment. The holding piece can therefore be used to hold the implant within a housing during sterilisation, transportation and storage.

When the implant is to be used, the insertion tool can be connected to the holding piece via the tool retention means and the implant, together with the holding piece, can be removed from the housing. The at least one resilient element provides a firm connection between the holding piece and implant during transfer of the implant with the insertion tool to the implant site. At the implant site the implant is inserted into the bone with the aid of the insertion tool. After insertion of the implant into the bone the insertion tool is pulled back. The holding piece is designed such that the retentive force of the connection between the holding piece and the insertion tool is greater than the retentive force of the connection between the holding piece and the implant. This characteristic causes the connection between the implant and the holding piece to disconnect first when the practitioner pulls back the insertion tool after having inserted the implant into the implant site. The holding piece remains connected to the insertion tool. In effect therefore, once the insertion tool has been connected to the holding piece these two components function as a single element throughout the implantation procedure. In this way removal of the holding piece from the implant is facilitated and the practitioner can immediately continue with the surgical procedure. Only a single, simple step is required to remove both the holding piece and the insertion tool. The holding piece can later be removed from the insertion tool, which can then be reused.

The retentive force of a specific connection is the minimal force required to disconnect said connection. The at least one resilient element is adapted to provide a retention force of preferably between 1 and 10N, more preferably between 1 and 5N. The retentive force provided by the tool retention means is greater than the chosen retentive force of the resilient element but is preferably no greater than 20N. Preferably the difference between the first and second retentive forces is at least 1N, more preferably at least 5N.

The one or more resilient elements firmly connect the implant to the holding piece during the course of various events such as sterilisation, packing, transportation, storage and insertion.

A resilient element is one whose shape can be distorted or otherwise adjusted but which returns to its original shape after removal of the distorting force. This quality allows the element to be bent, compressed or otherwise displaced in order to enable relative movement between the implant and holding piece, but then to spring back to, or at least towards, its original position in order to hold the implant on the holding piece until the element is again distorted to allow removal of the implant.

An example of a suitable resilient element is an o-ring or other elastic, compressible component. The use of an elastic component is however less preferred as the high flexibility of such components renders them an unsuitable material from which to manufacture the whole of the holding piece. Therefore a holding piece comprising an o-ring or other elastic resilient element must necessarily be composed of two separate components. This increases the cost and complexity of the holding piece.

It is therefore preferable for the at least one resilient element to be an integral part of the holding piece. Most preferably the at least one resilient element is a flexible arm bendable in a direction perpendicular to the longitudinal axis of the holding piece. This enables the arm to be flexed towards or away from the longitudinal axis. Although the flexible arm may simply provide a clamping fit with the implant, it is preferable that the arm comprises a catch feature shaped to engage a complementary feature of an implant. In this way the at least one resilient element creates a "snap fit" connection with the implant.

Snap fit connections are well known in the art and refer to the displacement and subsequent release of a resilient element upon alignment of the element with a complementary structure that allows the element to return to its original, or near original, form. The sudden release of the resilient element results in a physical and sometimes aural feedback to the user that the connection has been made.

The snap connection between the implant and the holding piece is preferably designed in such a way that the holding piece can again be connected to the implant after the connection was initially disconnected. Reconnecting the holding piece to the implant can be useful in case the implant was not correctly inserted in the bone, e.g. positioned too high or deep. Therefore the resilient element is preferably configured such that it can be disconnected from the implant without permanent distortion or damage. This is also beneficial from a safety perspective as it prevents the possibility of parts of the holding piece breaking off in the patient's mouth.

The at least one flexible arm of the holding piece may be arranged to engage the exterior or interior of a dental implant. The chosen design of the flexible arm(s) will depend to a large extent on the implant design with which the holding piece will be used.

For example, many implants, in particular implants intended for use with a separate abutment component, comprise an internal bore extending longitudinally into the implant from the coronal end. The bore can comprise a radial groove or rib, or undercut. A holding piece designed to connect to such internal implant geometry can therefore comprise at least one flexible arm comprising, on its radially outer side, a catch feature shaped to engage this internal complementary feature of an implant. The catch feature can comprise either a complementary radially protruding nub or regressed indent shaped to engage the internal feature of the implant. The bore of the implant may also comprise an apical threaded portion and/or an anti-rotation feature. This anti-rotation feature can be used to prevent relative rotation between the implant and an abutment but can also be used to transmit torque to the implant during insertion into the bone. The complementary feature of the bore, for snap connection to the holding piece, can be provided separately to these features or may be a part of either of these structures.

Alternatively, an external snap connection can be formed. In such cases the exterior of the implant must comprise an indentation or protrusion for co-operation with the catch feature of the flexible arm(s). In one advantageous configuration the implant is formed with an undercut. For example, the implant may comprise an outwardly tapering portion which extends to an outer perimeter, thus forming a collar or shoulder. The flexible arm(s) can therefore be shaped to complement this collar such that the arm engages the implant below the outer perimeter. Alternatively the implant may comprise an external anti-rotation feature, located on the coronal end of the implant, or an integrally formed abutment part. Either of these features may comprise an undercut, groove or protrusion that can be complemented by the catch feature of the flexible arm(s). In this embodiment therefore, the catch feature is located on the radially inner side of the at least one flexible arm for engagement with an external complementary feature of an implant.

The holding piece preferably comprises two, more preferably four flexible arms arranged to form a snap connection with the interior or exterior of an implant, wherein the arms are arranged in mutually opposing pairs. Furthermore, the retentive force provided by the flexible arms should be sufficient to support the implant without need of any additional elements. In this way, the implant is preferably in contact only with the holding piece when held in the housing and is not in direct contact with the housing itself, whereby contamination of the implant by the material of the housing is avoided and sterilization is facilitated. In order to increase the retentive force provided by the flexible arms at least two of these can be connected at their distal ends, such that a partial or complete annular ring is formed.

Preferably the at least one resilient element is arranged to connect to an area of the implant which will not be in direct contact with the bone after insertion. This will of course always be the case when the resilient element is arranged to connect to an internal feature of the implant. When an external connection is made this preferably occurs at the coronal end of the implant, e.g. with the abutment part of a one-part implant, external anti-rotation feature or neck portion of a two-part implant. Other areas therefore, in particular more sensitive areas such as the bone contact surface, experience no contact with the holding piece or the housing.

The first end of the holding piece preferably further comprises a support collar arranged for abutment with the implant. This provides additional support to the implant and prevents pivotal movement of the implant relative to the holding piece, which may result in the disconnection of the resilient element(s) from the implant. In order to reduce the contact between the implant and holding piece the support collar is preferably discontinuous in that it consists of a plurality of longitudinally extending struts, the struts forming an abutment surface for contacting the implant. These abutment surfaces do not provide any axial retention, which is provided solely by the at least one resilient element. The described construction allows a safe retention of the implant, although only a small area of the implant is in contact with the holding piece, thus allowing a thorough sterilization of the implant. The holding piece is thus arranged in such a way that the surface of the implant, which is in contact with the holding piece, is reduced to a minimum while still ensuring reliable holding properties.

In embodiments in which the arms are adapted for internal connection to an implant, the struts are formed radially outwards of the flexible arms. The struts and arms may however be located at the same angular location, such that each arm has an associated strut. It is also possible of course for the holding piece to comprise differing numbers of flexible arms and struts.

In embodiments in which the arms are adapted for external connection to an implant, the struts are preferably formed by the flexible arms. Therefore, in one embodiment the at least one flexible arm comprises, at its proximal end, an abutment surface for contacting the implant. When the arm comprises a catch feature the abutment surface should be proximal of this catch feature.

During the steps related to the insertion of an implant, such as removing the implant from the housing, transferring the implant to the implant site and inserting the implant into the bone, an insertion tool is connected to the tool retention means of the holding piece.

A firm connection between the insertion tool and the holding piece is important, to prevent dropping of the implant. This is clearly highly undesirable, as this can result in damage and contamination of the implant or aspiration of the implant by the patient. In accordance with the present invention the retentive force between the holding piece and the insertion tool is greater than the retentive force between the holding piece and the implant, in order to enable the insertion tool and holding piece to be jointly removed from the inserted implant.

Hence, the tool retention means of the holding piece is adapted to interact with a securing portion of the insertion tool in order to provide a secure connection. The holding piece acts as a connector between the implant and the insertion tool and hence no direct axial retention occurs between the insertion tool and the implant.

In accordance with another aspect of the present invention therefore there is provided an insertion tool for cooperation with a holding piece as described herein. The insertion tool comprises a distal end, having a torque transmission element, and a shank, the shank comprising a securing portion for engagement with the holding piece.

The engagement between the holding piece and the insertion tool can be based on a thread, press fit, friction fit, snap connections or the use of an o-ring or a griper.

Therefore, for example, the tool retention means of the holding piece may comprise a male threaded shaft and the securing portion of the insertion tool may comprise a complementary female threaded cavity, or vice versa.

In an alternative embodiment the connection between the tool retention means and insertion tool may comprise a bayonet fixture. In such an embodiment the tool retention means or the securing portion comprises one or more radially extending protrusions while the other component comprises a cavity containing one or more helically extending grooves. The insertion tool can thus be connected to the holding piece by rotating the insertion tool such that the protrusions are guided along the helical grooves. The holding piece and insertion tool will then remain connected until relative rotation occurs in the opposite direction.

However, preferably the connection between the holding piece and insertion tool comprises at least one resilient element, which can be positioned on either the holding piece or insertion tool.

In a similar manner to the connection between the holding piece and the implant, the resilient element of the tool retention means may comprise an o-ring or other elastic element. However, again this would require the elastic element to be provided separately and hence increases the number of components necessary.

Therefore preferably the tool retention means is an integral part of the holding piece and more preferably comprises at least one flexible arm bendable in a direction perpendicular to the longitudinal axis of the holding piece. This enables the arm(s) to be flexed towards or away from the longitudinal axis. Although the resilient arm may simply provide a clamping fit with the insertion tool it is preferable that the arm comprises a catch feature shaped to engage a complementary feature of the insertion tool so as to create a "snap fit" connection with the insertion tool.

Therefore preferred embodiments of the present invention comprise snap connections between the holding piece and implant and the holding piece and the insertion tool. Preferably, there is no radial movement of the insertion tool necessary to form the snap connections but only effort in the axial direction. In turn the snap connections are preferably disengaged by effort in the opposite axial direction. In this embodiment no threads are required and no tedious screwing is needed to form or break the connection between the holding piece and the insertion tool/implant.

Although it is possible to reverse the snap connection between the holding piece and the insertion tool, such that the at least one flexible arm is formed by the securing portion of the insertion tool and the complementary feature by the tool retention means of the holding piece, it is preferable for the flexible arm to be located on the holding piece. This is particularly true when both the resilient element and the tool retention means comprise flexible arms, as this enables both elements to be integrally formed on the holding piece. In addition, the holding piece can be formed of a suitably flexible material while enabling the insertion tool to be formed of a stronger, less flexible material.

Preferably the tool retention means is located at the second end of the holding means, such that the housing connection segment is located between the first end and the tool retention means. This eases access to the tool retention means by the insertion tool when the holding piece is held within the housing.

Providing an integral holding piece that enables a simple, non-rotational connection to both an implant and insertion tool is considered inventive in its own right and therefore, viewed from a further aspect therefore the present invention comprises a holding piece for an implant comprising a first end and a second end, both ends arranged on a longitudinal axis, and in between the two ends a housing connection segment for connecting the holding piece to a housing for the implant. The first end comprises at least one integrally formed flexible arm bendable in a direction perpendicular to the longitudinal axis for connecting the first end to an implant. The second end comprises at least one integrally formed flexible arm bendable in a direction perpendicular to the longitudinal axis and adapted to directly connect the holding piece to an insertion tool.

Preferably, as mentioned previously, the at least one flexible arm of the first end comprises a catch feature shaped to engage a complementary feature of an implant and the at least one flexible arm of the tool retention means comprises a catch feature shaped to engage a complementary feature of an insertion tool such that a snap fit connection can be formed between the holding piece and an implant and the holding piece and an insertion tool.

In accordance with one aspect of the present invention, the snap fit connection between the holding piece and the insertion tool must have a greater retentive force than that between the holding piece and the implant. This can be achieved in numerous ways. For example, the flexible arm(s) of the tool retention means may be shorter and/or thicker than the arm of the resilient element(s). A greater force is therefore needed to displace these. Alternatively, or in addition, the depth of the engaging feature into which the flexible arm "snaps" can be greater in relation to the tool retention means. This requires the flexible arm to be more greatly displaced in order to disconnect the insertion tool and the holding piece. The shape of the catch feature also influences the retentive force. It is preferable that the catch feature of at least the tool retention means comprises a barb. A barb is formed by a tapered, curved or otherwise gradated surface which ends in an abrupt step change in diameter such that an abutment surface is formed. This enables the arm to flex with relative ease in order to allow passage of the insertion tool in one direction (i.e. towards the holding piece) but to resist movement of the tool in the opposite direction once the catch has been engaged.

The connection between the holding piece and the insertion tool can be made either with the exterior or interior of the insertion tool.

When the connection is to be formed with the interior of the insertion tool the tool retention means is arranged for insertion into a blind or thorough bore of the insertion tool. For example, the at least one flexible arm of the preferred tool retention means can be arranged for insertion into a blind bore of the insertion tool and comprise a catch feature on its radially outer side. The surface of the blind bore comprises a complementary feature for engaging the catch feature of the flexible arms in a snap connection.

In a preferred embodiment however the connection is formed on the exterior of the insertion tool. Therefore, in this embodiment the second end of the holding means defines an interior space for housing the distal end of an insertion tool. This interior space may be defined exclusively by multiple flexible arms which form the tool retention means. Alternatively the second end may comprise a closed annular ring, in which one or more flexible arms are formed, for example by milling or injection moulding. The flexible arms of the tool retention means may also be located away from the second end, in which case the interior space must extend far enough into the holding piece to allow the insertion tool to reach and engage with the arms. The one or more flexible arms can comprise, on their radially inner side, a catch feature. In this embodiment the securing portion of the insertion tool comprises a groove or other complementary feature formed on the exterior surface of the tool which is shaped to engage the catch feature of at least one flexible arm to form a snap connection.

In this embodiment the diameter of the interior space defined by the second end is equal to the largest outer diameter of the distal end of the insertion tool introduced into the holding piece.

This embodiment is preferred as the introduction of the insertion tool into the interior space of the holding piece provides additional strength to the holding piece. This in turn allows the holding piece to be made of a relatively soft material, such as plastics. This reduces the cost of the component.

In a particularly preferred embodiment the holding piece comprises lateral openings in the exterior surface of the holding piece which connect to the interior space defined by the second end. Preferably, when the first end comprises a plurality of flexible arms the lateral openings are formed, at least in part, between these arms.

Preferably the holding piece is hollow. This reduces the weight of the holding piece and the material required to manufacture this. This embodiment features free space in the interior of the holding piece, which free space preferably is available in the first and second ends for the construction of the snap connections with the implant and the insertion tool. In other words, the free space enables the flexible arms to bend inward.

In a preferred embodiment the holding piece has substantially the shape of a cylinder, preferably the shape of a circular cylinder, so that the shape of the holding piece is designed substantially as a hollow cylinder.

Providing a holding piece having an at least partially hollow interior with lateral openings and/or providing a hollow holding piece enables the insertion tool, when connected to the holding piece, to protrude from the holding piece.

This is beneficial as it allows parts of the insertion tool to directly contact the implant. In the prior art discussed in detail above, the insertion tool is not in direct contact with the implant and hence torque must be transferred to the implant via the holding element or carrier screw. This requires these components to be manufactured such that a good force transmitting connection can be achieved. In addition the components must be strong enough to withstand the torque placed on them during use and to transmit this effectively to the implant.

A hollow or partially hollow holding piece in accordance with the present invention however allows the insertion tool to pass through the holding piece for direct connection with the implant. In this way, all or part of the torque can be transferred directly to the implant by the insertion tool.

The insertion tool comprises, at its distal end, a torque transmission element. Although this element may to arranged to transfer torque to the holding piece, which in turn transmits this to the implant, this element is preferably arranged to protrude through the lateral openings or hollow first end of the holding piece for direct engagement with the implant.

In preferred embodiments therefore the holding piece does not comprise a force transmission element capable of transmitting torque to the implant. The holding piece therefore does not comprise a surface which, when an implant is connected to the first end, engages this implant in such a way that torque can be transmitted from the holding piece to the implant. In other words, the first end of the holding piece is arranged only to provide axial retention to the implant. All the torque is transmitted to the implant via the insertion tool. In this embodiment therefore the functions of axial retention and torque transmission are separated. The holding piece provides axial retention while the insertion tool transmits torque. As the holding piece does not need to withstand and transmit rotational forces this can be made of a lighter, weaker material than the insertion tool. Preferably the holding piece is formed of a plastic material such as PEEK, POH, PPSU, PSU, etc and can be manufactured via, for example, injection moulding. The holding piece can therefore be manufactured simply, more cheaply and with tighter tolerances than a holding piece designed for torque transmission, as such a holding piece must be formed of metal or metal alloy.

In accordance with this preferred embodiment, the single use holding piece can be cheaply produced and provided with every implant while a multiple use insertion tool is provided separately.

The separation of the functions of axial retention and torque transmission is considered inventive in its own right and therefore, viewed from a further aspect, the present invention provides a holding piece for an implant comprising a first end and a second end, both ends arranged on a longitudinal axis, and in between the two ends a housing connection segment for connecting the holding piece to a housing for the implant. The first end comprises at least one resilient element for connecting to an implant and the holding piece further comprises tool retention means adapted to directly connect the holding piece to an insertion tool, wherein the holding piece does not comprise a force transmission element for transferring torque to an implant.

Viewed from another aspect the present invention provides a holding piece in combination with an insertion tool, said holding piece comprising a first end and a second end, both ends arranged on a longitudinal axis, and in between the two ends a housing connection segment for connecting the holding piece to a housing for the implant. The first end comprises at least one resilient element for connecting to an implant. The holding piece further comprises tool retention means adapted to directly connect the holding piece to the insertion tool. The insertion tool comprises a distal end, having a torque transmission element, and a shank, the shank comprising a securing portion for engagement with the tool retention means. The holding piece is at least partially hollow such that the torque transmission element of the insertion tool can be inserted into and protrude from the holding piece for direct engagement with the implant.

Preferably the torque transmission means of the insertion tool is arranged to provide all of the torque to the implant. Preferably the holding piece is arranged to provide the sole means of axial retention between the implant and insertion tool.

The holding piece is preferably hollow such that it forms a hollow cylinder extending from the first end to the second end. In this embodiment therefore the insertion tool can extend through the holding piece such that, when the holding piece is connected to the insertion tool, the torque transmission element is exposed and can contact the anti-rotation means of the implant directly. Alternatively the holding piece may be at least partially hollow such that the second end defines an interior space, said interior space connecting to lateral openings in the exterior of the holding piece. In this embodiment the torque transmission element may be arranged to extend through said lateral openings when the holding piece is connected to the insertion tool.

The torque transmission element of the insertion tool is shaped to engage an anti-rotation element of the implant. The torque is usually applied by the practitioner to the insertion tool with or without the aid of additional tools, such as a wrench, ratchet, or dental handpiece which can be connected to the insertion tool.

The torque transmission element may comprise, for example, one or more polygon sections, such as hexagonal or octagonal polygon sections. Said polygon sections interact with anti-rotation means having a corresponding shape on the implant. In some embodiments the torque transmission element may comprises a male or female polygon shape for inserting into or receiving the anti-rotation means of an implant.

In a preferred embodiment the torque transmission element comprises at least one longitudinally extending groove, preferably at least two, most preferably four. These grooves are configured to engage protrusions formed in an interior bore of an implant. Preferably, said at least one groove comprises two lateral faces substantially parallel to the longitudinal axis. These faces are arranged to transmit torque to the side faces of protrusions in the implant. Alternatively the torque transmission element could comprise at least one longitudinally extending protrusion configured to engage a groove of the implant in a similar manner.

In embodiments in which the holding piece comprises flexible arms for connection to the interior of the implant the grooves of the insertion tool are further shaped to house these arms when the tool is inserted into the holding piece, the grooves extending radially beyond these arms for direct engagement with the implant.

In embodiments in which the holding piece comprises flexible arms for connection to the exterior of the implant, the torque transmission element of the insertion tool need not protrude longitudinally past these arms but only through the main body of the holding piece such that it can engage the anti-rotation feature of the implant.

In an alternative embodiment both the insertion tool and the holding piece are arranged to provide torque transmission to the implant. In this embodiment the holding piece may comprise lateral openings to allow protrusion of the torque transmission element of the insertion tool and additionally comprise, adjacent to these openings, at least one torque transmission surface for direct engagement with the anti-rotation means of the implant. The torque transmission elements of the holding piece and insertion tool in this embodiment may comprise only fractions of polygon sections which, when the holding piece and the insertion tool are connected, form a complete polygon. Alternatively both the insertion tool and the holding means may comprise longitudinally extending grooves for engagement with protrusions in the implant or protrusions for engagement with grooves in the implant.

According to this embodiment the rotational forces that must be applied to the implant are distributed between the holding piece and the insertion tool. In such embodiments the holding piece must be made of a relatively strong material, for example TAN (titanium aluminium nitride) or TAV (titanium aluminium vanadium), in order to transmit toque to the implant. This allows the flexible arms to be thicker and provide stronger retentive forces to the implant and insertion tool. As the insertion tool must extend through the holding piece at least until the torque transmission surface the insertion tool adds strength to the holding piece.

The holding piece is preferably made of injection plastics, or metal or metal alloy, such as titanium, TAN or TAV. A holding piece made of plastics is preferable, particularly when the holding piece plays no or a minimal part in torque transmission.

The holding piece according to the present invention is preferably made completely of a single material. The production of the holding piece is therefore facilitated as compared to prior art. As a consequence production costs of the holding piece, which is preferably shipped as a disposable article, are lower.

The holding piece according to the present invention is preferably made of a single, integral piece. The production of the holding piece made of a single piece is greatly facilitated as compared to the production of a carrier screw and a transfer piece, for example, or transfer piece and o-ring. Therefore the production costs of said holding piece are reduced. Also, a single piece holding piece allows a good sterilization.

According to another aspect the present invention provides a housing comprising the holding piece as described herein, the holding piece being removeably connected to the housing by the housing connection segment.

The housing according to the present invention preferably is of cylindrical or tubular shape, for example a cylinder with a cuboid or a circular or elliptic base, and comprises a longitudinal axis. The housing preferably has one or more lateral openings and/or at least one face is at least substantially open facilitating sterilization of the implant and the housing. The housing is dimensionally stable and is preferably made of COC, PEEK, PPSU etc. Thereby, the housing provides protection to the implant from damage or contamination. The housing is provided with a fixing section which is intended to cooperate with the housing connection segment of the holding piece. The housing connection segment is preferably fixed to the fixing section of the housing via press fit, friction fit, snap connections or bayonet mechanism or a combination thereof.

In a preferred embodiment of the housing the fixing section comprises a laterally open indent. Preferably the indent is in the form of a slot, which widens in the radial direction towards the lateral area and constricts towards the longitudinal axis. However, at the approximate location of the longitudinal axis the indent widens again to form a cut-out with a cross-section of about the shape of the cross-section of the housing connection segment of the holding piece. The holding piece can be laterally pressed into the indent and after the cross-section of the housing connecting segment has overcome the width of the constriction, the housing connecting segment latches into the cut-out. In order to remove the implant from the housing the insertion tool is usually connected to the tool retention means of the holding piece. Then the implant together with the holding piece is laterally pulled out of the housing.

The housing connection segment of the holding piece therefore comprises, in this embodiment, a cylindrical outer wall. This can be bordered in the longitudinal direction by portions of the holding piece which have a greater diameter. The housing connection segment may have a diameter similar to that of the implant, i.e. no greater than 5 mm.

In a preferred embodiment the fixing section of the housing induces increased pressure on the at least one resilient element of the holding piece, thus providing an increment of the retentive force required to disconnect the connection between the implant and the holding piece during transportation and storage. It should be noted however that the first retentive force of the holding piece refers to the inherent retentive force, i.e. that produced solely by the at least one resilient element.

In another embodiment, in which the resilient element forms an internal connection to the implant, the housing further comprises a pin element. During transportation and storage the pin element is inserted into the holding piece such that the pin element is in contact with at least part of the resilient element of the holding piece. The pin element either presses the resilient element(s) towards the surface of the implant or simply prevents these from flexing inwards. In this way the implant is more securely held within the housing. The pin may be configured such that it only contacts the holding piece, or this may also contact the implant interior. When the implant is to be removed from the housing, the pin element is removed. The insertion tool is then connected to the holding piece and the implant is removed.

In a further preferred embodiment the pin element is part of a closure cap for the housing.

The holding piece is usually provided to the practitioner as part of a combination comprising a housing, the holding piece and a dental implant. The implant is held within the housing by means of the holding piece, the at least one resilient element connecting the first end of the holding piece to the implant.

In a preferred embodiment, for inserting the implant to the implant site the distal end of the insertion tool is inserted into the holding piece such that the tool retention means engages the securing portion of the insertion tool. Then, the implant together with the holding piece is removed from the housing with the aid of the insertion tool. Subsequently, the insertion tool together with the implant and the holding piece is transferred to the implant site followed by inserting the implant into the bone. For insertion of the implant, torque is applied to the insertion tool, and the torque is transmitted by the torque transmission element to the implant, preferably directly. After complete insertion of the implant into the implant site the insertion tool is usually pulled back along the direction of the longitudinal axis. The connection between the implant and the holding piece is disconnected and the connection between the holding piece and the insertion tool remains. The insertion tool finally is removed from the implant site after which the holding piece can be separated from the insertion tool. This can be done either by overcoming the retentive force or by destroying the holding piece, e.g. by cutting.

In one embodiment as discussed above the insertion tool transmits the torque directly to the implant.

According to a further aspect the present invention comprises a combination of the holding piece and insertion tool described above.

According to another aspect the present invention comprises a holding piece in combination with an implant, said holding piece comprising a first end and a second end, both ends arranged on a longitudinal axis, and in between the two ends a housing connection segment for connecting the holding piece to a housing for the implant. The first end comprises at least one resilient element connected to the implant, such that the implant is retained with a first retentive force. The holding piece further comprises tool retention means adapted to directly connect the holding piece to an insertion tool with a second retentive force that is greater than the first retentive force.

In one embodiment the implant comprises an internal bore, the at least one resilient element being connected to said internal bore.

In another embodiment the implant comprises an undercut on its exterior, the at least one resilient element being connected to the undercut.

Preferably the implant further comprises anti-rotation means, wherein said holding piece does not engage said anti-rotation means in a torque transmitting manner.

According to a further aspect the present invention comprises a combination of the housing, holding piece, insertion tool and implant as detailed above.

BRIEF DESCRIPTION OF THE DRAWINGS

Further characteristics and advantages of the present invention are described with the help of the accompanying drawings, wherein

FIG. 4A shows a lateral view of an assembly consisting of an insertion tool according to the present invention, the holding piece of FIG. 3A and a dental implant;

FIG. 4B shows a cross sectional view along line A-A of the assembly depicted in FIG. 4A;

FIG. 4C shows a detail B of the assembly depicted in FIGS. 4A and 4B;

FIG. 8A shows a perspective view of a further embodiment of the holding piece of the present invention; and FIG. 8B shows a perspective view of a further embodiment of an insertion tool according to the present invention, for use with the holding piece of FIG. 8A.

DETAILED DESCRIPTION

Figure 1A:
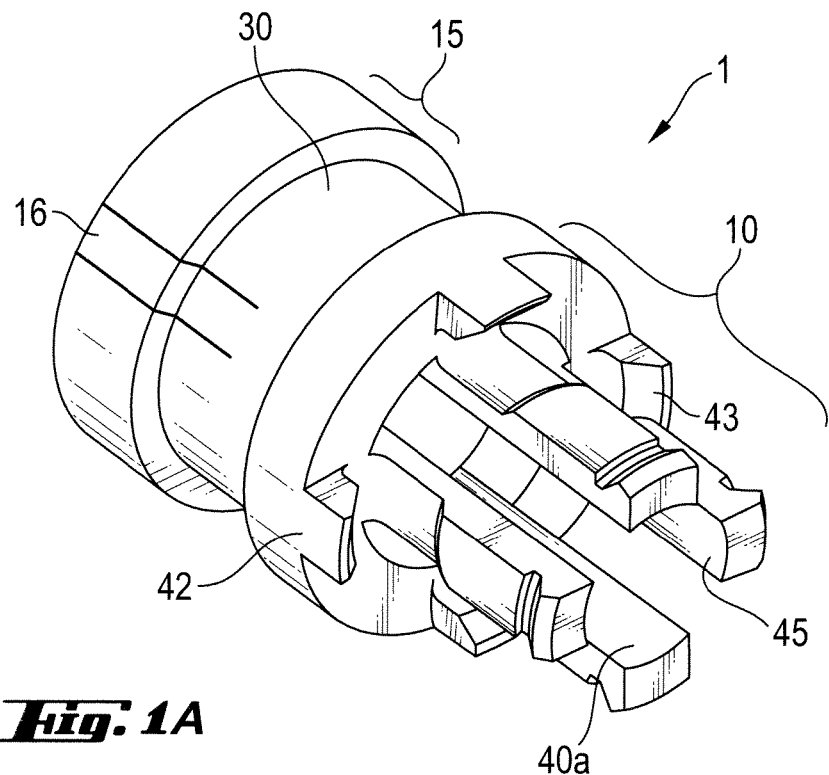
FIG. 1A shows a perspective view of a holding piece according to a first embodiment of the present invention.
Figure 1B:
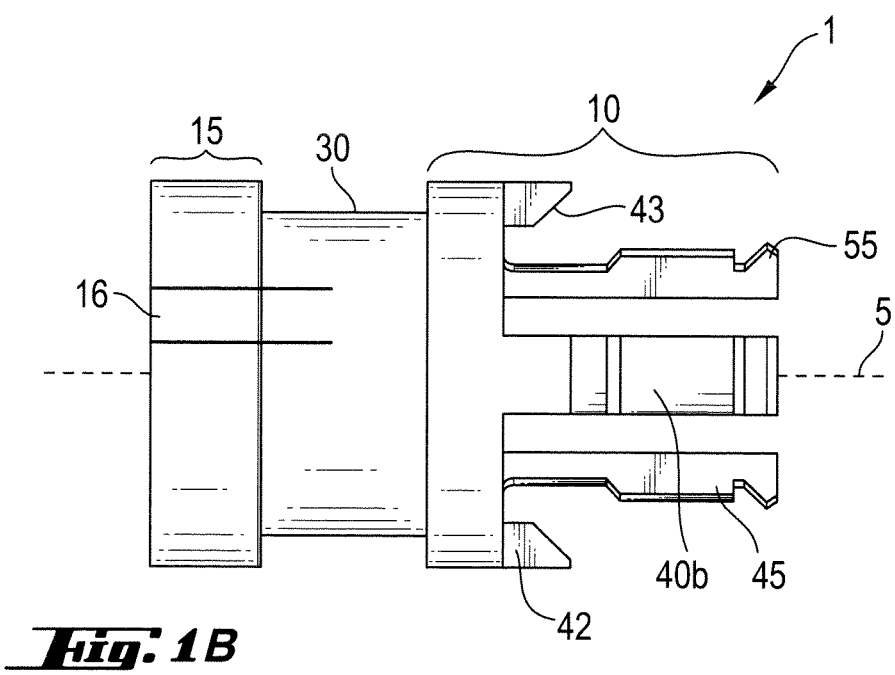
FIG. 1B shows a lateral view of the holding piece depicted in FIG. 1A.

FIGS. 1A and 1B show a preferred embodiment of a holding piece 1 according to the present invention. The holding piece 1 has a longitudinal axis 5 and substantially a circular cylindrical shape. The holding piece 1 exhibits a through hole along the longitudinal axis 5 and thus substantially has a shape of a hollow cylinder. The holding piece 1 comprises a first end 10 and a second end 15 opposite to the first end 10 along the longitudinal axis 5. The second end 15 comprises a tool retention means adapted to cooperate directly with an insertion tool 20 (not shown in FIG. 1) with the aid of a securing portion. The first end 10 is intended to be connected to a dental implant 25 (not shown in FIG. 1).

Between the first end 10 and second end 15 the holding piece 1 exhibits a housing connection segment 30, which is used to connect the holding piece 1 to a housing 35 (not shown in FIG. 1) for the dental implant 25. The housing connection segment 30 has a circular cylindrical shape and is to be fixed to the housing 35 in a press-fit manner.

The holding piece 1 shown in FIG. 1A and FIG. 1B is made of a single, integral piece. No further pieces are required to connect the holding piece 1 to the implant 25 or to the insertion tool. The holding piece 1 shown in FIG. 1 is intended for single use and is made of injection plastics.

The production of the holding piece 1 shown in FIG. 1 is greatly facilitated as it is made of only one piece, consists of a single material and is preferably produced in one step.

The first end 10 of the holding piece 1 comprises four resilient elements in form of four flexible arms 45 extending parallel to the longitudinal axis 5. These arms 45 are bendable towards and away from the longitudinal axis 5. The flexible arms 45 are intended to be inserted inside a blind bore 50 of the dental implant 25. Near the distal end of each of the arms 45 is a snap catch 55 intended to form a snap connection with the internal connection of the implant 25.

The shown embodiment further comprises longitudinally extending struts 42 near the lateral area of the first end 10. Said struts 42 form a discontinuous support collar and are intended to further stabilize the implant 25 when connected to the holding piece 1. The struts 42 each comprise an abutment surface 43 which is arranged, when the holding piece 1 is connected to the implant, to abut against an outer surface of the implant. This prevents any pivoting of the implant with respect to the holding piece 1.

The tool retention means comprises two mutually opposing flexible arms 16. As with arms 45, the flexible arms 16 of the tool retention means can bend towards and away from the longitudinal axis 5.

Holding piece 1 is designed in such a way that torque can be directly transmitted from the insertion tool 20 to the dental implant 25. The hollow shape of the holding piece 1 allows the insertion tool 20 to penetrate the holding piece 1 and to interact with the implant 25 directly.

The interaction between the holding piece 1, implant 25 and insertion tool 20 is demonstrated by FIGS. 2A-D.

These figures show an assembly 60 of a dental implant 25, the holding piece 1 of FIGS. 1A-B and insertion tool 20. The assembly 60 comprises the anchoring part (implant) of a two-piece dental implant having internal connection means in the form of a blind bore 50 extending into the implant 25 from the coronal end 65. This blind bore 50 comprises a thread at its apical end (not shown) and, coronally of said thread, protrusions 95 which form an anti-rotation means. Said assembly 60 for instance is formed after the insertion tool 20 has been inserted into the second end 15 of the holding piece 1, and the implant 25 was removed from the housing 35 with the aid of the insertion tool 20. The assembly 60 is now to be transferred to the implant site, for example.

The insertion tool 20 comprises a shank 105. The shank 105 features, at one end, connecting means 110 for connecting the insertion tool 20 to further tools such as a wrench or a ratchet. The distal end 75 of the insertion tool 20 is inserted into the second end 15 of the holding piece 1, which is itself attached to the implant 25. For simplicity, FIG. 2B does not detail the connections between the holding piece 1 and the implant and insertion tool. These are instead shown in FIG. 2C.

Figure 2A:
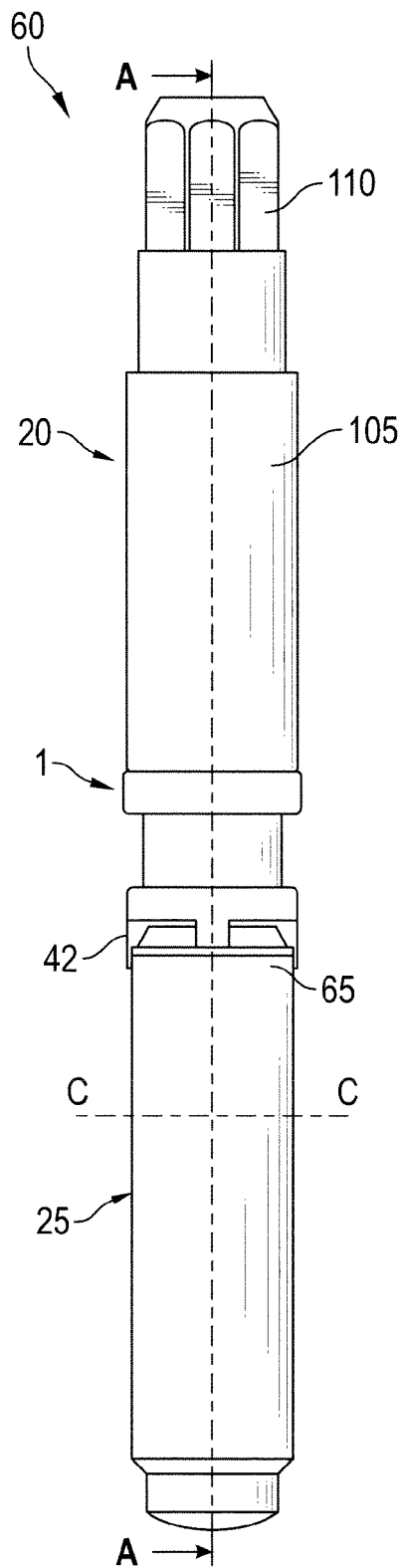
FIG. 2A shows a lateral view of an assembly consisting of an insertion tool according to the present invention, the holding piece of FIG. 1A and a dental implant.

In the connected state the flexible arms 45 of the first end 10 form a snap connection with the implant 25, wherein each snap catch 55 engages with an annular groove 100 located inside the blind bore 50 of the dental implant 25. Struts 42 contact the external surface of the coronal end 65 of the implant 25. As can clearly be seen in FIG. 2C, the abutment surfaces 43 are shaped to match the outer contour of the coronal end 65 such that the abutment surfaces 43 support the implant 25 but do not provide any axial retention. The axial retention is provided solely by flexible arms 45 and their snap connection to the internal bore 50. As can be seen in FIG. 2A, the spacing between struts 42 allows easy circulation of sterilising fluids. During transportation and storage the implant is connected only to the holding piece 1, which in turn is fastened within housing 35, as will be discussed in relation to FIG. 6.

When the implant 25 is to be removed from the housing 35, the distal end 75 of the insertion tool 20 is inserted through the hollow second end 15 of the holding piece 1. Distal end 75 comprises a securing portion in the form of an annular groove 22. This groove 22 co-operates with the flexible arms 16 of the tool retention means in order to connect the insertion tool 20 firmly to the holding piece 1. As can be seen in FIG. 2C, flexible arms 16 comprise, on their radially inner side, catch features 24 in the shape of barbs. When the distal end 75 of the insertion tool 20 is inserted into the second end 15 of the holding piece, flexible arms 16 bend outwards. When the barbs are aligned with groove 22, they "snap" into this groove 22, providing a physical and aural feedback that the insertion tool has been fully inserted. The barbed nature of the catch features 24 increases the force necessary to disconnect the insertion tool 20 from the holding piece 1. The retentive force of the connection between the holding piece 1 and the insertion tool 20 is greater than the retentive force of the connection between the dental implant 25 and the holding piece 1.

The distal end 75 of insertion tool 20 has a circular cylindrical shape and, in addition to annular groove 22, comprises four grooves 80 substantially parallel to the longitudinal axis of the insertion tool. These grooves form the torque transmission element of the insertion tool 20, which in this embodiment forms the only means of torque transmission to the implant 25.

The distal end 75 of the insertion tool 20 is inserted into the holding piece 1. The grooves 80 of the torque transmission element are aligned with the flexible arms 45 of the first end 10 such that, in the connected state, these arms 45 are partially situated within the grooves 80. Arms 45 extend beyond the distal end 75 of the insertion tool 20 however in order to co-operate with the annular groove 100 of the implant 25, as discussed above. The internal bore 50 of the implant 25 comprises, coronally above the groove 100, anti-rotation means in the form of longitudinally extending protrusions 95, or guide rails. This can be more clearly seen in FIG. 2D.

Each groove 80 of the torque transmission element has two lateral faces 85 substantially parallel to the longitudinal axis 5. The grooves 80 have a greater depth than the height of the portions of the flexible arms 45 which are situated within the grooves 80. This means that the lateral faces 85 of the groove 80 protrude beyond the flexible arms 45 such that the end portions 90 can directly contact the anti-rotation protrusions 95 of the implant 25.

The lateral faces 85 of the grooves 80 thus act as torque transmission means and transmit torque from the insertion tool 20 directly to the dental implant 25. In this way the plastic holding piece 1 does not need to transmit the high torque forces to the implant 25. Instead this component only provides an indirect axial connection between the implant 25 and the insertion tool 20.

Figure 3A:
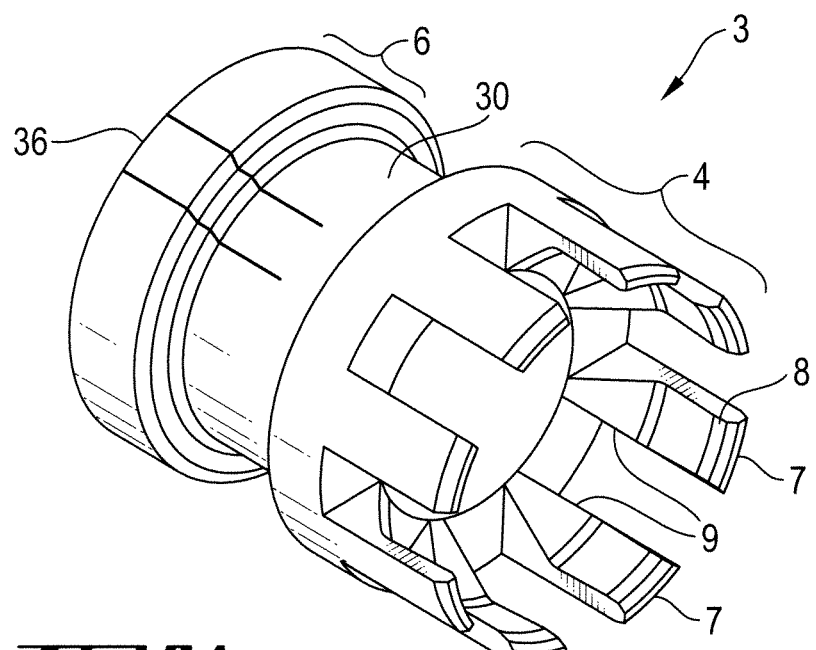
FIG. 3A shows a perspective view of a holding piece according to a further embodiment of the present invention.
Figure 3B:
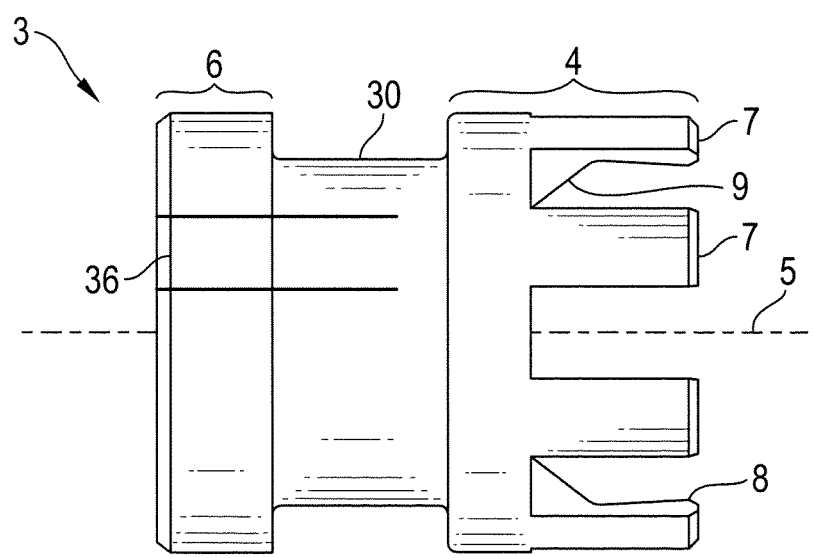
FIG. 3B shows a lateral view of the holding piece depicted in FIG. 3A.

FIGS. 3A and 3B show an alternative holding piece 3. This is identical to the holding piece of the previous figures in terms of operation, except that this is designed to connect to the exterior of the implant 25.

The holding piece 3 has a longitudinal axis 5 and substantially a circular cylindrical shape. The holding piece 3 exhibits a through hole along the longitudinal axis 5 and thus substantially has a shape of a hollow cylinder. The holding piece 3 comprises a first end 4 and a second end 6 opposite to the first end 4 along the longitudinal axis 5. The second end 6 comprises a tool retention means adapted to cooperate directly with an insertion tool 23 with the aid of a securing portion. The first end 4 is intended to be connected to a dental implant 25.

Between the first end 4 and second end 6 the holding piece 3 exhibits a housing connection segment 30, which is used to connect the holding piece 3 to a housing 35. The housing connection segment 30 has a circular cylindrical shape and is to be fixed to the housing 35 in a press-fit manner.

The first end 4 of the holding piece 3 comprises eight resilient elements in form of flexible arms 7 extending parallel to the longitudinal axis 5. These arms 7 are bendable towards and away from the longitudinal axis 5. The flexible arms 7 are intended to connect to the exterior the dental implant 25. Near the distal end of each of the arms 7 is a snap catch 8 intended to form a snap connection with the implant 25.

The arms 7 further comprise, proximal of the catch 8, abutment surfaces 9. Said abutment surfaces 9 form a discontinuous support collar and are intended to further stabilize the implant 25. It can thus be seen that, in effect, the struts 42 of the previous embodiment have been incorporated into the flexible arms. This is possible as, due to the external snap connection used in this embodiment, the flexible arms 7 are positioned radially outwards of the arms 45 of the previous embodiment.

The tool retention means of the second end 6 comprise two mutually opposing flexible arms 36, identical to the tool retention means of the previous embodiment.

The interaction between the holding piece 1, implant 25 and insertion tool 23 is demonstrated by FIGS. 4A-C. In this embodiment, the implant 25 is identical to that of FIG. 2.

Figure 2B:
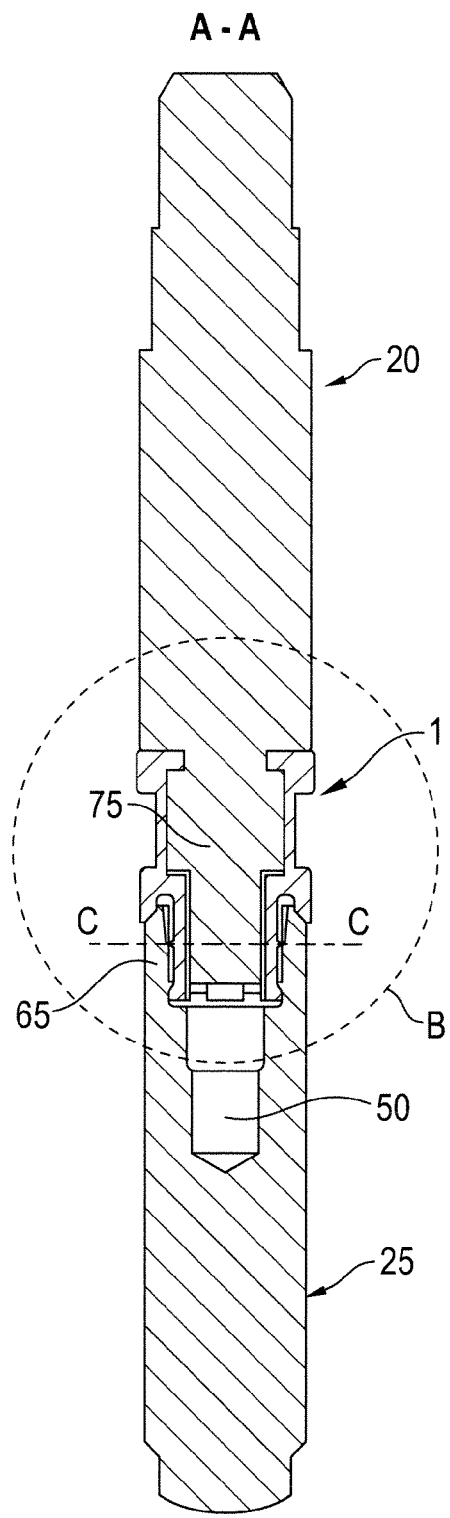
FIG. 2B shows a cross sectional view along line A-A of the assembly depicted in FIG. 2A.
Figure 2C:
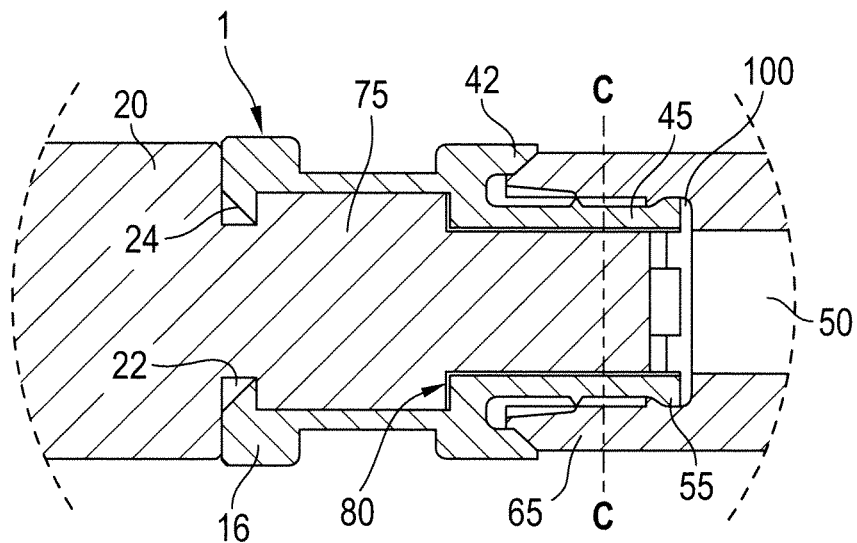
FIG. 2C shows a detail B of the assembly depicted in FIGS. 2A and 2B.
Figure 2D:
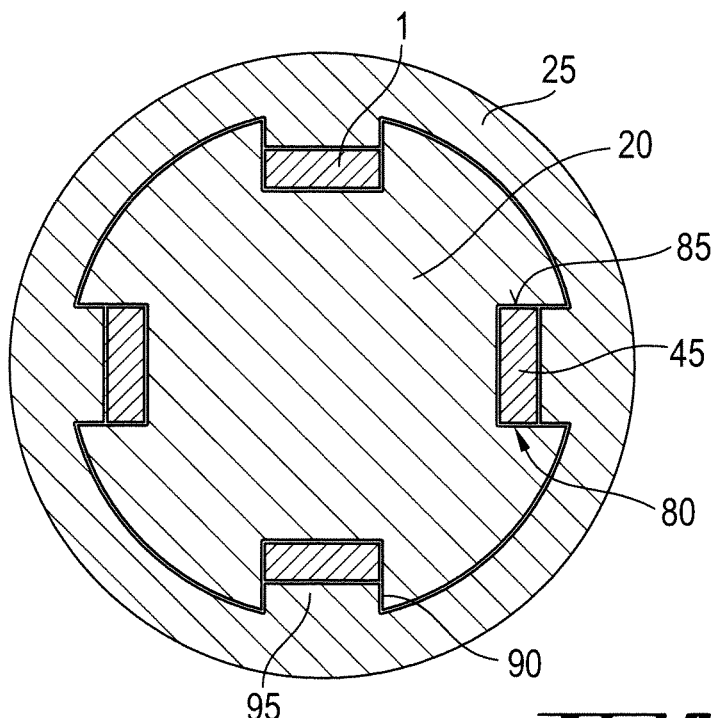
FIG. 2D shows a cross sectional view along line C-C shown in FIGS. 2A and 2B perpendicular to the longitudinal axis.

As with FIGS. 2A-C, these figures show an assembly 60 of a dental implant 25, the holding piece 3 and insertion tool 23.

The insertion tool 23 comprises a shank 205. The shank 205 features, at one end, connecting means 210 for connecting the insertion tool 23 to further tools such as a wrench or a ratchet. The distal end 31 of the insertion tool 23 is inserted into the holding piece 3, which is itself attached to the implant 25. The connections between the holding piece 3 and the implant and insertion tool are best seen in FIG. 4C.

In the connected state the flexible arms 7 of the first end 4 form a snap connection with the exterior of the implant 25. The coronal end 65 of the implant includes an undercut, formed by an outwardly tapering section 26. The snap catches 8 are shaped in a complementary manner to the undercut such that the flexible arms 7 form a snap connection to the implant 25. Abutment surfaces 9 contact the external upper surface of the coronal end 65 of the implant 25 but do not provide any axial retention. As can be seen in FIG. 4A, the spacing between arms 7 allows easy circulation of sterilising fluids. During transportation and storage the implant is connected only to the holding piece 3, which is fastened within housing 35, as will be discussed in relation to FIG. 6.

When the implant 25 is to be removed from the housing 35, the distal end 31 of the insertion tool 23 is inserted through the hollow second end 6 of the holding piece 3. Distal end 31 comprises a securing portion in the form of an annular groove 32. This groove 32 co-operates with the flexible arms 36 of the tool retention means in order to connect the insertion tool 23 firmly to the holding piece 3. As can be seen in FIG. 4C, flexible arms 36 comprise, on their radially inner side, catch features 34 in the shape of barbs, which operate as described in relation to FIG. 2C. The retentive force of the connection between the holding piece 3 and the insertion tool 23 is greater than the retentive force of the connection between the dental implant 25 and the holding piece 3.

Figure 5:
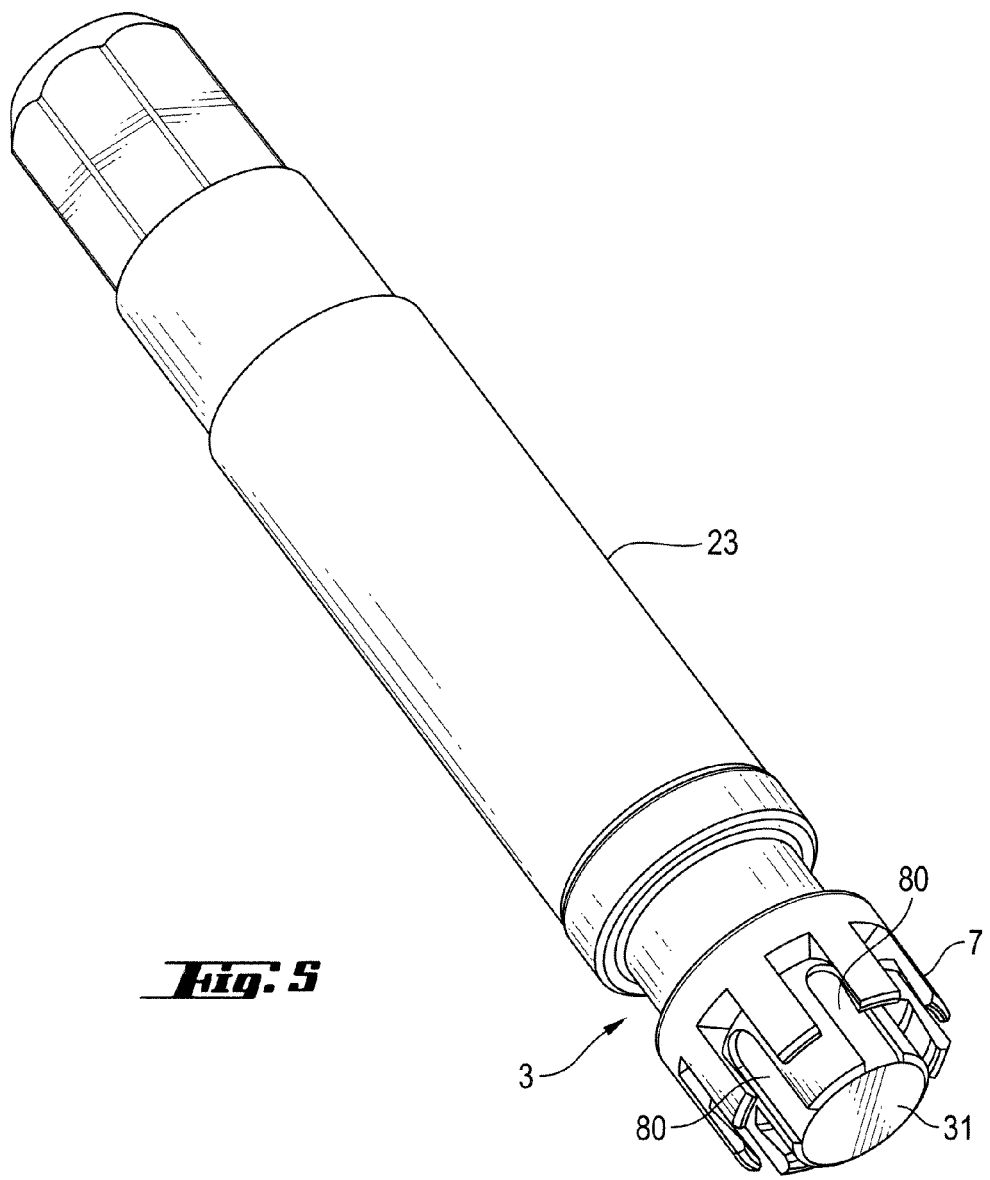
FIG. 5 shows a perspective view of the holding piece and insertion tool of FIGS. 4A-C in combination but separate from the implant.

The distal end 31 of insertion tool 23 has a circular cylindrical shape and, in addition to annular groove 32, comprises four grooves 80 substantially parallel to the longitudinal axis of the insertion tool. These grooves form the torque transmission element of the insertion tool 23, which in this embodiment forms the only means of torque transmission to the implant 25. The torque transmission element is best seen in FIG. 5, which shows the holding piece 3 attached to the insertion tool 23 but without the implant 25. This figure shows therefore how the assembly would look after the implant 25 has been inserted into the bone and disconnected from the holding piece 3.

The distal end 31 of the insertion tool 23 is inserted into and through the holding piece 3. The grooves 80 of the torque transmission element protrude through hollow holding piece 3 to enable direct engagement with the implant 25. Due to the lack of internal flexible arms the grooves 80 of insertion tool 23 do not need to be as deep as those of insertion tool 20. Each groove 80 has two lateral faces 85 substantially parallel to the longitudinal axis 5 which in use contact the lateral edges of protrusions 95 of the implant 25. Torque applied to the insertion tool 20 is thus transmitted from the insertion tool 20 directly to the implant 25.

Figure 6:
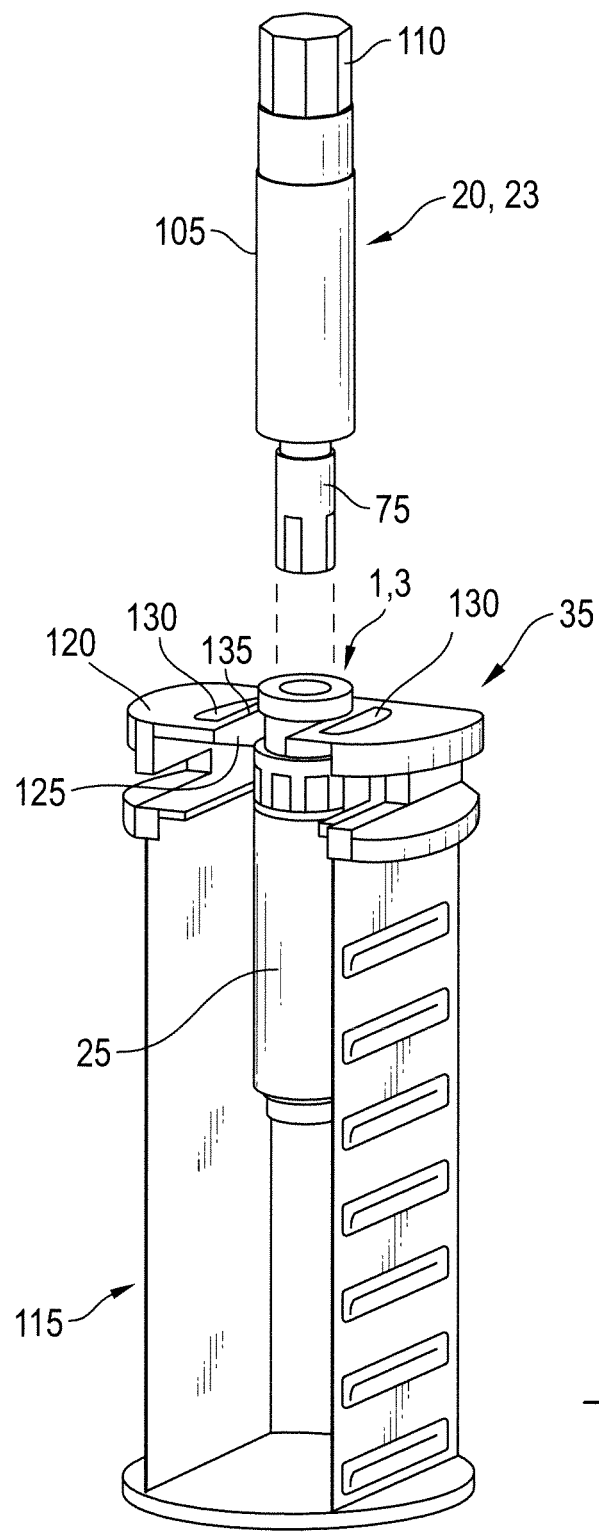
FIG. 6 shows a dental implant connected to a holding piece according to the present invention inside a housing according to the present invention.

FIG. 6 shows a housing 35 according to the present invention. The housing is preferably made of COC, PEEK, PPSU etc and comprises a holding piece 1, 3 and a dental implant 25. The housing 35 substantially has a tubular shape. The body 115 of the housing 35 substantially is hollow for accommodating the body of the implant 25, wherein one face of the housing 35 is open allowing access to the implant 25. The open face facilitates sterilization of the implant and the housing. On a front end the housing 35 further features a fixing section 120 for connecting the holding piece 1, 3 to the housing 35.

The dental implant 25 is connected to the housing 35 via the holding piece 1, 3. The dental implant 25 is connected to the first end 10, 4 of the holding piece 1, 3 as discussed above. The housing connection segment 30 is connected to the fixing section 120 of the housing 35. The fixing section 120 preferably comprises a laterally open indent 125 and, on both sides of the indent 125, cut-outs 130 on the front end of the housing 35. A flexible flap 135 is formed between the indent 125 and the cut-outs 130. The indent 125 is in principle in the form of a slot, which in radial direction widens towards the lateral area and constricts towards the longitudinal axis of the housing. The housing connection segment 30 of the holding piece 1 is fixed in the indent 125 in a clamping manner between the two flexible flaps 135.

The insertion tool 20, 23 about to be connected to the implant 25 is shown in FIG. 6. The distal end of the insertion tool 20, 23 is being inserted into the second end 15, 6 of the holding piece 1, 3. The holding piece 1, 3 is connected to the housing 35 in such a way that the implant 25 is accommodated inside the free space of the housing 35 and that the second end 15, 6 is accessible easily from the outside of the housing 35.

Figure 7:
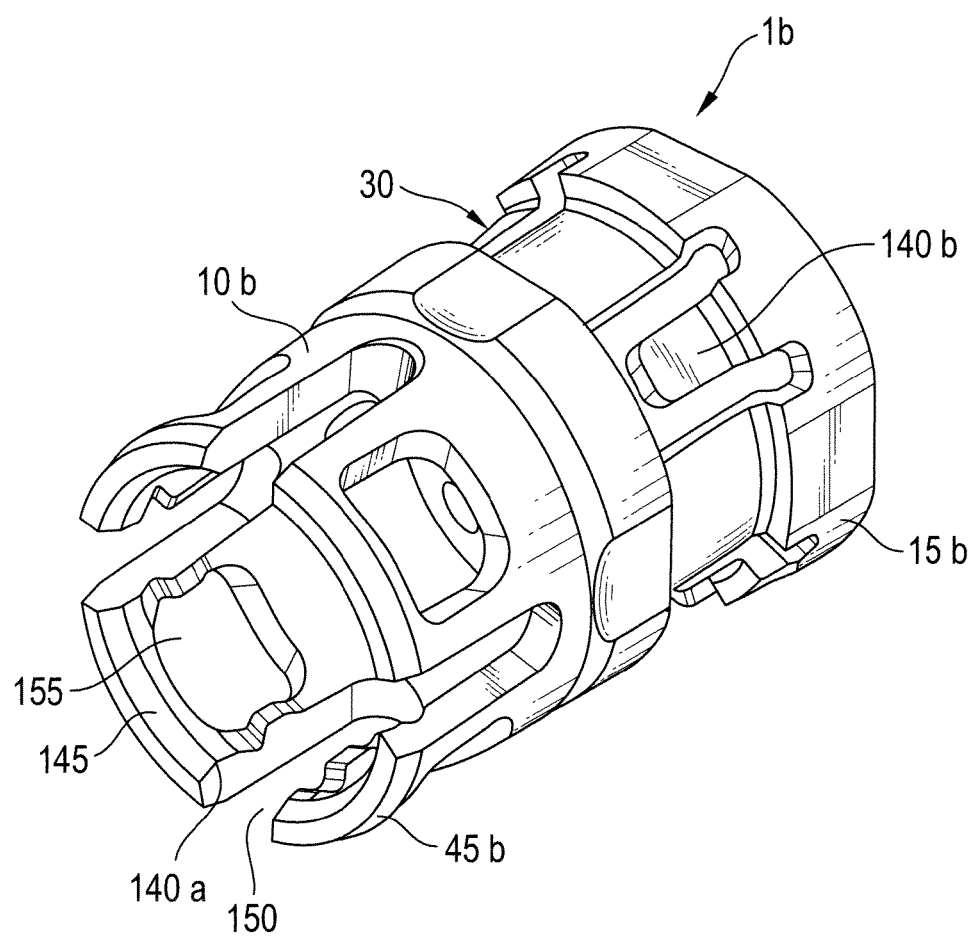
FIG. 7 shows a perspective view of another embodiment of the holding piece according to the present invention.

FIG. 7 shows a perspective view of another embodiment of the holding piece 1b. The first end 10b of the holding piece 1b comprises four flexible arms 45b. Alternatively these can be viewed as eight flexible arms, with each second pair being connected at their distal end, thus forming a discontinuous annular ring. Each flexible arm 45b features catch feature 140a, for forming a snap connection with the exterior of an implant. A one- or two-piece dental implant can be to be supported and retained by this holding piece 1b.

The second end 15b comprises flexible arms 140b, which constitute part of the snap connection for connecting the holding piece 1b to a insertion tool. The retentive force of the connection between the tool receiving section 15b and the insertion tool is greater than the retentive force of the connection between the dental implant and the implant receiving section 10b.

In the above described embodiments it is the insertion tool that transmits torque directly to the implant.

FIGS. 8A and 8B show a further embodiment in which torque transmission is provided by both the insertion tool and the holding piece.

Holding piece 11 is formed in the shape of a hollow cylinder. First end 12 comprises two flexible arms 13 for snap connection to the interior of an implant 25. Second end 14 once again comprises arms 17 for connection to the groove 27 of insertion tool 21 (see FIG. 8B). In a similar manner to the previous embodiments holding piece 11 comprises a housing connection segment 30. In addition to providing a snap connection to the implant, flexible arms 13 also comprise, on their radially outer sides, grooves 19.

The distal end 18 of the insertion tool 21 comprises torque transmission element in the form of two mutually opposing grooves 80. The distal end 18 can be inserted through the hollow holding piece 11 such that the arms 17 engage the groove 27 in a snap connection. When the insertion tool 21 is connected to the holding piece 11 in this way the force transmission element is aligned with the flexible arms 13 such that grooves 80, 19 engage protrusions 95 of the implant 25. In this way, both the holding piece 11 and the insertion tool 21 transmit torque to the implant 25.

The above described embodiments are for illustrative purposes only and the skilled man will realize that many alternative arrangements are possible which fall within the scope of the claims.

The invention claimed is:

1. Holding piece for an implant comprising a first end and a second end, both ends being arranged on a longitudinal axis, and in between the two ends a housing connection segment for connecting the holding piece to a housing for the implant, wherein the first end comprises at least one resilient element, which is arranged to connect to an internal feature of the implant, said at least one resilient element being adapted to retain the implant with a first retentive force, the holding piece further comprising tool retention means adapted to directly connect the holding piece to an insertion tool with a second retentive force that is greater than the first retentive force, the tool retention means comprising flexible arms having, on their radially inner side, catch features in the shape of barbs, such that disengagement of the implant from the holding piece is achieved solely by pulling back the holding piece along the direction of the longitudinal axis to overcome the first retentive force while the barbs provide the second retentive force, greater than the first retentive force, securing the holding piece to the tool,
wherein the holding piece is at least partially hollow, such that the insertion tool may pass through the holding piece for direct connection with the implant.

2. Holding piece as claimed in claim 1, wherein the at least one resilient element is an integral part of the holding piece.

3. Holding piece as claimed in claim 2, wherein the at least one resilient element is a flexible arm bendable in a direction perpendicular to the longitudinal axis of the holding piece.

4. Holding piece as claimed in claim 3, wherein the arm comprises a catch feature shaped to engage a complementary feature of an implant such that a snap fit connection can be formed between the holding piece and the implant.

5. Holding piece as claimed in claim 4, wherein the catch feature is positioned on the radially outer side of the at least one flexible arm for engagement with an internal complementary feature of the implant.

6. Holding piece as claimed in claim 3, wherein the at least one flexible arm further comprises, at its proximal end, an abutment surface for contacting the implant.

7. Holding piece as claimed in claim 1, wherein the first end further comprises a support collar arranged for abutment with the implant.

8. Holding piece as claimed in claim 7, wherein the support collar consists of a plurality of longitudinally extending struts, said struts forming an abutment surface for contacting the implant.

9. Holding piece as claimed in claim 1, wherein the tool retention means is an integral part of the holding piece.

10. Holding piece as claimed in claim 9, wherein the flexible arms of the tool retention means are bendable in a direction perpendicular to the longitudinal axis of the holding piece.

11. Holding piece as claimed in claim 10, wherein the barb shaped catch feature of the tool retention means is shaped to engage a complementary feature of the insertion tool so as to create a snap fit connection with the insertion tool.

12. Holding piece as claimed in claim 1, wherein the second end defines an interior space for housing the distal end of the insertion tool.

13. Holding piece as claimed in claim 12, further comprising lateral openings in the exterior surface of the holding piece which connect to the interior space defined by the second end.

14. Holding piece as claimed in claim 13, wherein the holding piece does not comprise a force transmission element for transmitting torque to the implant.

15. Holding piece as claimed in claim 1, wherein the holding piece is hollow.

16. Insertion tool in combination with a holding piece for an implant, the holding piece comprising
a first end and a second end, both ends being arranged on a longitudinal axis,
and in between the two ends a housing connection segment for connecting the holding piece to a housing for the implant,
wherein the first end comprises at least one resilient element, which is arranged to connect to an internal feature of the implant, said at least one resilient element being adapted to retain the implant with a first retentive force,
the holding piece further comprising tool retention means adapted to directly connect the holding piece to the insertion tool with a second retentive force that is greater than the first retentive force, the tool retention means comprising flexible arms having, on their radially inner side, catch features in the shape of barbs, such that disengagement of the implant from the holding piece is achieved solely by pulling back the holding piece along the direction of the longitudinal axis to overcome the first retentive force while the barbs provide the second retentive force, greater than the first retentive force, securing the holding piece to the tool,
wherein the holding piece is at least partially hollow, such that the insertion tool may pass through the holding piece for direct connection with the implant,
the insertion tool comprising a distal end having a torque transmission element and a shank, the shank comprising a securing portion for engagement with the tool retention means of the holding piece.

17. Insertion tool and holding piece as claimed in claim 16, wherein the securing portion comprises a complementary feature formed on the exterior surface of the tool, said complementary feature being shaped to engage the barbed shaped catch feature of the holding piece to form a snap connection.

18. Insertion tool and holding piece as claimed in claim 16, wherein the torque transmission element is arranged to protrude through the holding piece for direct engagement with an implant.

19. Insertion tool and holding piece as claimed in claim 18, wherein the torque transmission element is arranged to protrude through lateral openings in the holding piece.

20. Insertion tool and holding piece as claimed in claim 19, wherein the force transmission element comprises at least one longitudinally extending groove configured to engage protrusions formed in the interior bore of the implant.

* * * * *